(12) United States Patent
Page et al.

(10) Patent No.: US 11,865,338 B2
(45) Date of Patent: Jan. 9, 2024

(54) PROSTHESIS FUNCTIONALITY BACKUP

(71) Applicant: COCHLEAR LIMITED, Macquarie University (AU)

(72) Inventors: Rowan Christopher Page, Macquarie University (AU); Kenneth Oplinger, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 614 days.

(21) Appl. No.: 16/758,585

(22) PCT Filed: Oct. 22, 2018

(86) PCT No.: PCT/IB2018/058220
§ 371 (c)(1),
(2) Date: Apr. 23, 2020

(87) PCT Pub. No.: WO2019/082061
PCT Pub. Date: May 2, 2019

(65) Prior Publication Data
US 2020/0346013 A1    Nov. 5, 2020

Related U.S. Application Data

(60) Provisional application No. 62/575,571, filed on Oct. 23, 2017.

(51) Int. Cl.
*A61N 1/36* (2006.01)
*A61N 1/372* (2006.01)
*H04R 25/00* (2006.01)

(52) U.S. Cl.
CPC ..... *A61N 1/36038* (2017.08); *A61N 1/36031* (2017.08); *A61N 1/37247* (2013.01);
(Continued)

(58) Field of Classification Search
CPC .. H04R 25/55; H04R 25/558; H04R 2640/13; H04R 25/224; H04R 2225/61; H04R 2225/67
See application file for complete search history.

(56) References Cited

U.S. PATENT DOCUMENTS 6,816,600 B1    11/2004   Jakob et al.
7,373,204 B2    5/2008    Gelfand et al.
(Continued)

FOREIGN PATENT DOCUMENTS

CA    2911612 A1    10/2013
CN    102334347 A   1/2012
(Continued)

OTHER PUBLICATIONS

Office Action for China Patent Application No. 201880067957.4, dated Dec. 31, 2020.
(Continued)

*Primary Examiner* — Suhan Ni
(74) *Attorney, Agent, or Firm* — Pilloff Passino & Cosenza LLP; Martin J. Cosenza

(57) ABSTRACT

A body worn device, including a chassis and a functional suite supported by the chassis, wherein the device is configured to be worn on a recipient of a prosthesis, and the device is configured such that the functional suite automatically provides second functionality when the chassis is removed from the body of the recipient, the second functionality being related to the prosthesis.

22 Claims, 9 Drawing Sheets

(52) U.S. Cl.
CPC ......... *H04R 25/554* (2013.01); *H04R 25/558* (2013.01); *H04R 2225/61* (2013.01); *H04R 2225/67* (2013.01)

(56) References Cited

U.S. PATENT DOCUMENTS

| | | | |
|---|---|---|---|
| 7,639,828 | B2 | 12/2009 | Platz |
| 8,908,894 | B2 * | 12/2014 | Amento ............... H04R 25/554 381/151 |
| 9,510,112 | B2 | 11/2016 | Petersen et al. |
| 10,313,779 | B2 * | 6/2019 | Boesen ................ A61B 5/6803 |
| 11,272,367 | B2 * | 3/2022 | Milevski ............... H04W 12/08 |
| 2006/0204024 | A1 | 9/2006 | Eicher |
| 2008/0144867 | A1 | 6/2008 | Schulz |
| 2009/0226011 | A1 | 9/2009 | Abolfathi et al. |
| 2011/0144749 | A1 | 6/2011 | Kim et al. |
| 2013/0243227 | A1 | 9/2013 | Kinsbergen et al. |
| 2015/0119635 | A1 | 4/2015 | Gustafsson et al. |
| 2015/0126900 | A1 | 5/2015 | Walraevens et al. |
| 2015/0209591 | A1 | 7/2015 | Meskens |
| 2016/0089542 | A1 | 3/2016 | Frieding et al. |
| 2016/0144178 | A1 | 5/2016 | Hillbratt |
| 2016/0241975 | A1 | 8/2016 | Jensen et al. |
| 2017/0001008 | A1 | 1/2017 | Hunt et al. |
| 2017/0043161 | A1 | 2/2017 | Meskens |
| 2017/0064470 | A1 | 3/2017 | Popovac et al. |
| 2017/0143962 | A1 | 5/2017 | Mishra |
| 2017/0165487 | A1 | 6/2017 | van den Honert |
| 2017/0311092 | A1 | 10/2017 | Secall et al. |
| 2018/0235782 | A1 | 8/2018 | Choi et al. |

FOREIGN PATENT DOCUMENTS

| | | |
|---|---|---|
| CN | 104378845 A | 2/2015 |
| CN | 105072552 A | 11/2015 |
| CN | 105917673 A | 8/2016 |
| CN | 105934219 A | 9/2016 |
| CN | 205726417 U | 11/2016 |
| CN | 106797519 A | 5/2017 |
| CN | 206452547 U | 8/2017 |
| KR | 20090108373 A | 10/2009 |
| KR | 101585793 B1 | 1/2016 |
| WO | 2017069456 A1 | 4/2017 |

OTHER PUBLICATIONS

International Search Report and Written Opinion for PCT/IB2018/058220, dated Mar. 12, 2019.

Apple Support, "Use Live Listen with Made for iPhone hearing aids," https://support.apple.com/en-au/HT203990, accessed Apr. 23, 2020.

Luis Perez, "Apple Watch Review Roundup and Thoughts," Apr. 11, 2015.

* cited by examiner

PROSTHESIS FUNCTIONALITY BACKUP

CROSS-REFERENCE TO RELATED APPLICATIONS

This application claims priority to U.S. Provisional Application No. 62/575,571, entitled PROSTHESIS FUNCTIONALITY BACKUP, filed on Oct. 23, 2017, naming Rowan Christopher PAGE of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a body worn device, comprising a chassis, and a functional suite supported by the chassis, wherein the device is configured to be worn on a recipient of a prosthesis, and the device is configured such that the functional suite automatically provides second functionality when the chassis is removed from the body of the recipient, the second functionality being related to the prosthesis.

In accordance with another exemplary embodiment, there is a multiuse device, comprising a housing, and an operating system supported by the housing, wherein the multiuse device is configured to enable the housing to be supported by a human body at two different types of body parts, and the multiuse device is configured to interact with a medical device supported by the human body.

In accordance with another exemplary embodiment, there is a method, comprising utilizing a body wearable consumer electronics device as a head worn device to at least one of control or provide a signal to a prosthesis, and utilizing a processor in the body wearable device to perform functions unrelated to the prosthesis while wearing the device on a portion of the body other than the head.

BRIEF DESCRIPTION OF THE DRAWINGS

Embodiments are described below with reference to the attached drawings, in which.

DETAILED DESCRIPTION

Figure 1:
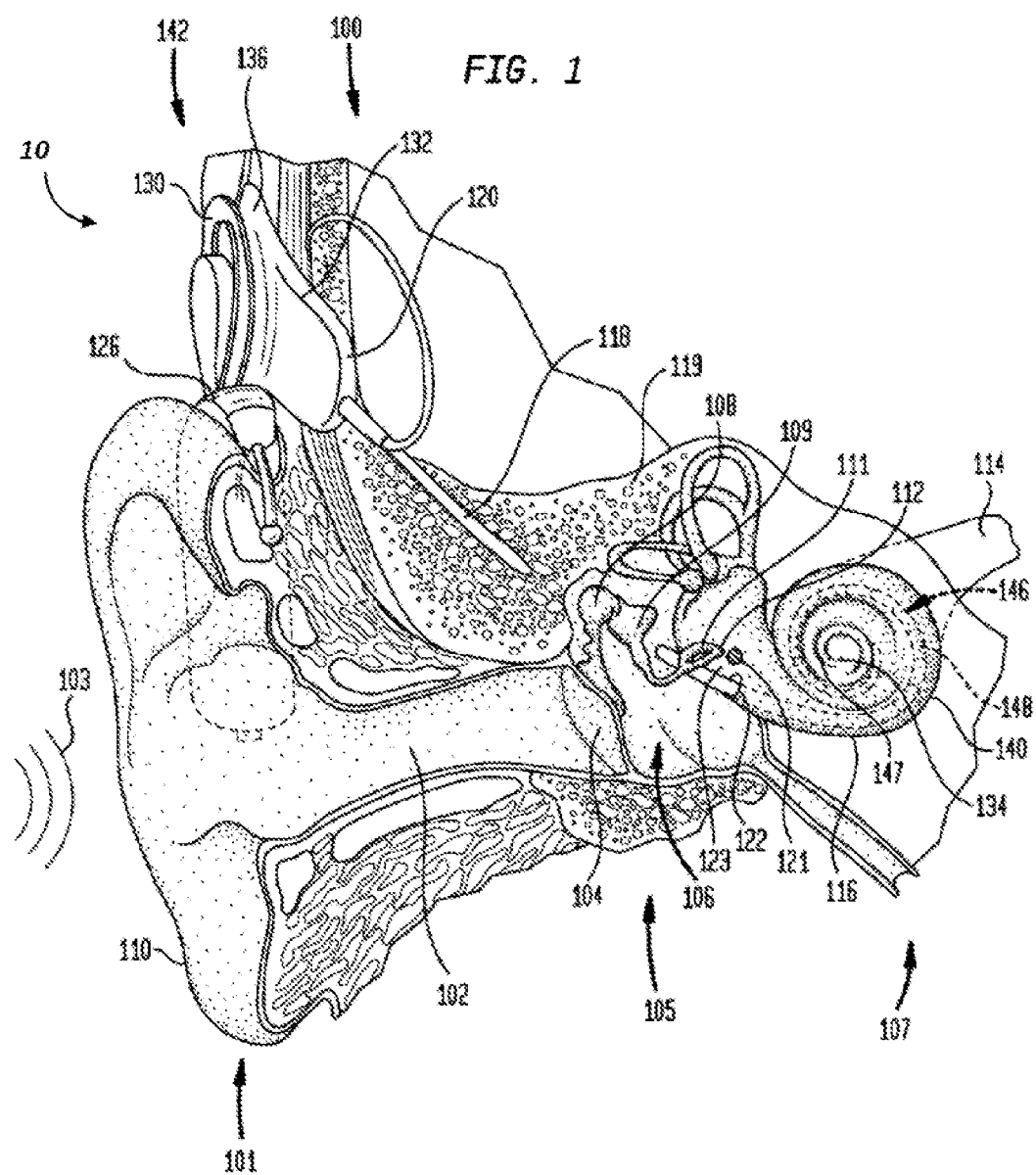
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, pacemakers, visual prostheses (e.g., bionic eyes), sensors, drug delivery systems, defibrillators, functional electrical stimulation devices, catheters, etc.

In view of the above, it is to be understood that at least some embodiments detailed herein and/or variations thereof are directed towards a body-worn sensory supplement medical device (e.g., the hearing prosthesis of FIG. 1, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 2:
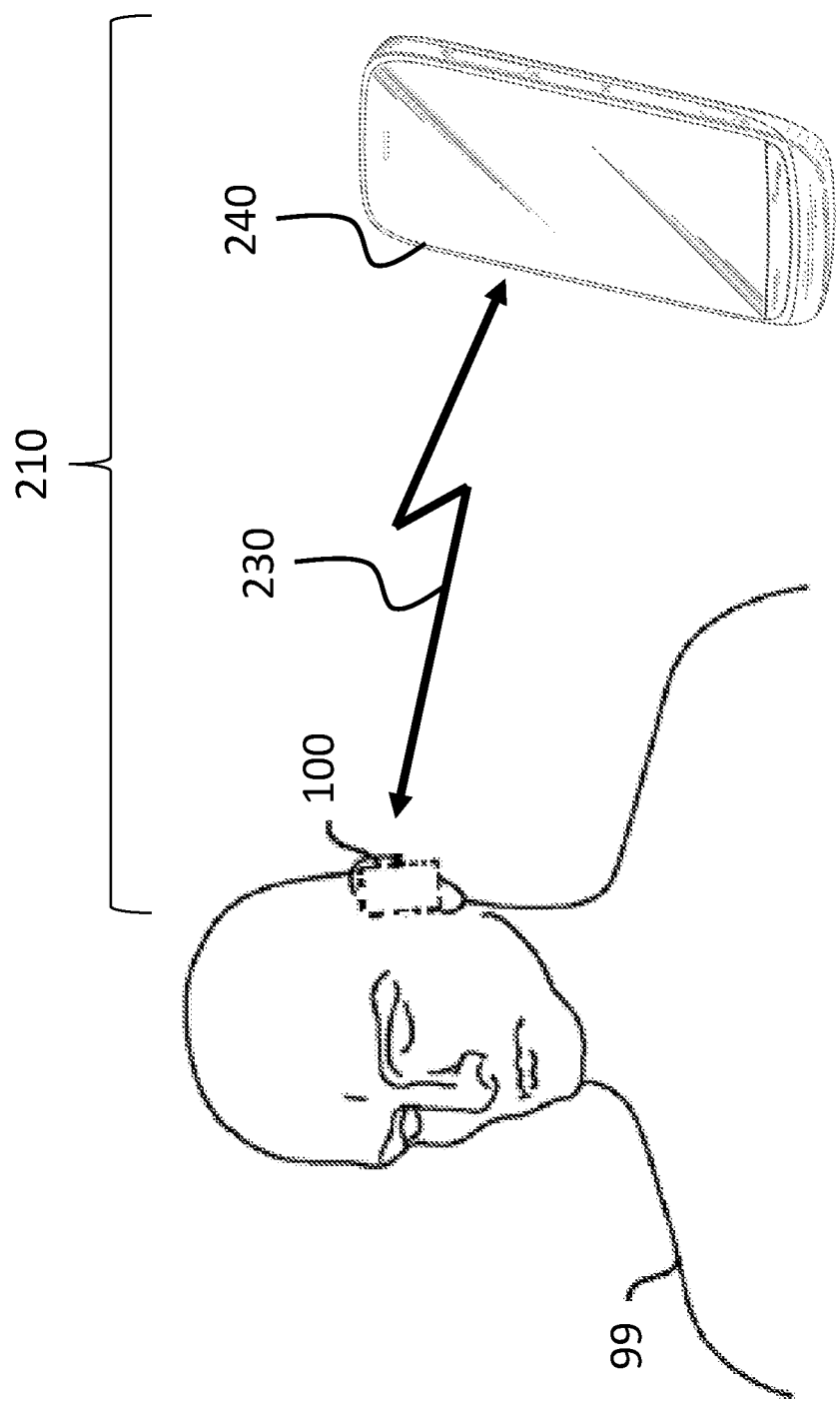
FIG. 2 presents an exemplary system including a hearing prosthesis and a remote device in the form of a portable hand-held device.

FIG. 2 depicts an exemplary system 210 according to an exemplary embodiment, including hearing prosthesis 100, which, in an exemplary embodiment, corresponds to cochlear implant 100 detailed above, and a portable handheld device 240 having a wireless link 230 with the hearing prosthesis 100. In an exemplary embodiment, the hearing prosthesis 100 is an implant implanted in recipient 99 (as represented functionally by the dashed lines of box 100 in FIG. 2). In an exemplary embodiment, the system 210 is configured such that cochlear implant 100 and the portable handheld device 240 (e.g., a portable cellular telephone, such as by way of example only and not by way of limitation, a smart phone, as that phrase is utilized generically) have a relationship. By way of example only and not by way of limitation, in an exemplary embodiment, the relationship is the ability of the smartphone to serve as a control device of the hearing prosthesis 100 via the wireless link 230 and/or to audio stream an audio signal captured by the microphone of the smartphone to the hearing prosthesis so the hearing prosthesis can evoke a hearing percept based on that audio stream (other relationships exist, as will be detailed).

Figure 3:
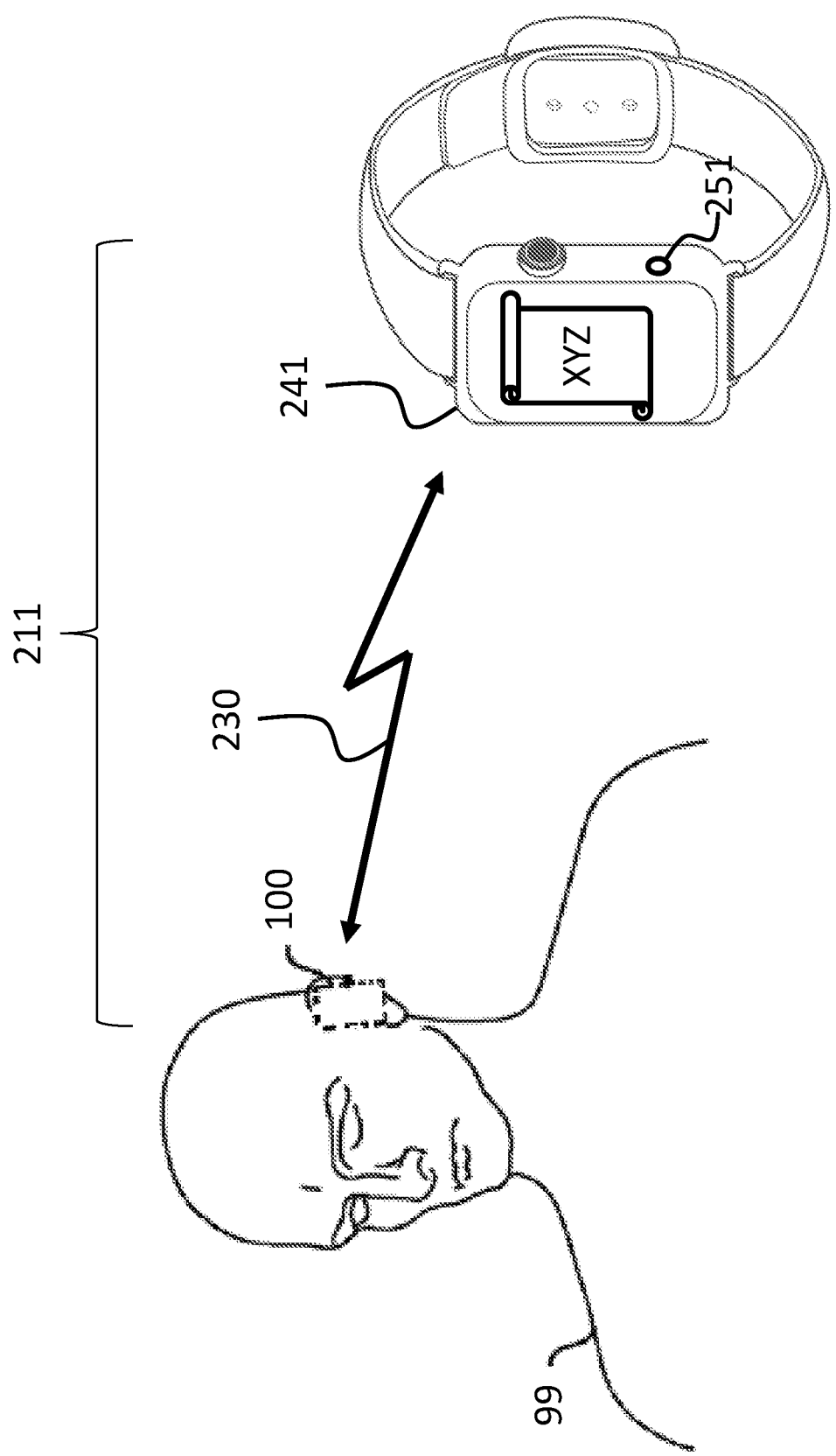
FIG. 3 presents an exemplary system including a hearing prosthesis and a body wearable consumer electronics device in the form of a smartwatch.

FIG. 3 depicts an exemplary system 211 according to an exemplary embodiment, including hearing prosthesis 100, which, in an exemplary embodiment, corresponds to cochlear implant 100 detailed above, and a portable device 241 having a wireless link 230 with the hearing prosthesis 100, where, here, the portable device 241 is a smartwatch. In an exemplary embodiment, the hearing prosthesis 100 is an implant implanted in recipient 99 (as represented functionally by the dashed lines of box 100 in FIG. 2). In an exemplary embodiment, the system 211 is configured such that cochlear implant 100 and the portable device 241 in the embodiment of a smart watch have a relationship. By way of example only and not by way of limitation, in an exemplary embodiment, the relationship is the ability of the smartwatch 241 to serve as a remote microphone for the prosthesis 100 via the wireless link 230.

In an exemplary embodiment, the system 210/211 is configured to enable the portable electronics device to reproduce the functionality of a given input device of the hearing prosthesis 100 (e.g., the input device is a button, a heat sensitive pad, etc., alone or in combination with another output device, such as an LED) at the portable electronics device. By way of example only and not by way of limitation, the input device could be a knob on the BTE device 126 that is adjusted by the recipient to increase or decrease the perceived volume of the resulting hearing percept evoked by the hearing prosthesis 100. The functionality of this knob thus being the control, or at least adjustment, of the perceived volume. In an exemplary embodiment, the hearing prosthesis is configured such that the portable electronics device has this functionality. Still further, in an exemplary embodiment, functions such as those that result in turning the processor of the hearing prosthesis on and off, changing maps of the hearing prosthesis and/or the initiation and/or halting of streaming are present in the portable electronics device.

In an exemplary embodiment, the body worn device 241, such as by way of example only and not by way of limitation, with respect to the embodiment of FIG. 3, the smartwatch, includes a chassis. This chassis, in some embodiments, can be a plastic and/or a metal chassis that supports such exemplary components as an LCD screen upon which images can be presented (e.g., text, pictures, graphics, etc.), where, in some embodiments, the LCD screen can be a touch screen, one or more microphones (e.g., 1, 2, 3, 4, 5, 6, 7, 8, 9, 10 or more microphones), one or more speakers (e.g., 1, 2, 3, 4, 5 or more speakers) and/or one or more vibrators, including the actuator(s) and counterweight(s) (if utilized) thereof, a central processing unit (CPU) which can be a computer chip or a computer processor, etc., one or more printed circuit boards, and lugs to which the watchband is attached, an RF transmitter, an RF receiver (e.g., a Wi-Fi and/or Bluetooth transmitter/receiver system), etc. It is noted that in at least some exemplary embodiments, the body worn device 241 corresponds to an Apple Watch™ Series 1 or Series 2, as is available in the United States of America for commercial purchase as of Jul. 4, 2017. In an exemplary embodiment, the body worn device 241 corresponds to a Samsung Galaxy Gear™ Gear 2, as is available in the United States of America for commercial purchase as of Jul. 4, 2017. In an exemplary embodiment, the aforementioned chassis carries one or more all of the components available in the just-detailed Samsung and/or Apple devices. It is noted that in at least some exemplary embodiments, the chassis is a single monolithic component, while in other embodiments, the chassis is an assembly of components integrated with respect to one another. It is noted that the body worn device can include two or more chassis.

To be clear, in at least some exemplary embodiments, the watch 241 is, in at least some exemplary embodiments, a wearable computer, that can run applications, utilizing an e operating system. The smart watch can function as a media player, with an FM radio and playback of digital audio and video files via Bluetooth and/or a USB headset (in some embodiments, the aforementioned chassis includes a USB port or another port to provide wired communication with the smartwatch and another component, such as by way of example only and not by way of limitation, the smart phone 240 and/or the hearing prostheses 100). In at least some exemplary embodiments, the watch 241 has full mobile phone capacity via an integrated cellular phone system suite, and is configured to make and/or answer phone calls and/or text messages.

In an exemplary embodiment, the watch 241 can include a touchscreen and a rechargeable battery and a digital camera and also includes a storage device, such as computer memory chips, etc. The watch 241 includes software and/or firmware that enables one or more all of the functionalities detailed herein to be executed.

It is briefly noted that any of the aforementioned features and/or the features detailed below of the smartwatch can also be present in the smart phone 240. Any disclosure herein of features associated with one also corresponds to a disclosure in an exemplary embodiment of those features being in the other, and vice versa.

In view of the above, it is to be understood that in at least some exemplary embodiments, the watch 241 includes a functional suite, and in some embodiments, this functional suite is supported by the chassis. The functional suite corresponds to any hardware and/or firmware and/or software that enables the smartwatch to function as a smartwatch, and thus can include the processor, the memory components (memory chips), etc.

It is noted that with respect to embodiments where element 241 is a smartwatch, it is to be understood that in some embodiments, the device is configured to be worn on a person, such as a recipient of the hearing prosthesis 100. By way of example only and not by way of limitation, in an exemplary embodiment, the hearing prosthesis 100 is implanted in and/or worn on the recipient, while the recipient is also wearing the watch 241 on his or her left or right wrist.

In an exemplary embodiment, the body worn device 241 is configured such that the aforementioned functional suite provides a first main functionality when the chassis is worn on a body of the recipient. In this regard, the functionality can correspond to any of the functionalities detailed above, such as by way of example only and not by way of limitation, any of the functionalities associated with the aforementioned watches detailed above available from the aforementioned manufacturers as of the aforementioned date detailed above. In an exemplary embodiment, the first functionality can of course be a smartwatch functionality. In an exemplary embodiment, such functionality can correspond to the provision of time to the recipient, the provision of text data to the recipient received from a remote location (an electronic text), the provision of an audio signal to the recipient (e.g., as a result from an incoming telephone call and/or as a result from a signal from a cellular phone (e.g., phone 240) that is in signal communication with the smart phone), the provision of the ability to take a digital picture (e.g., in the case where the smart phone includes a digital camera device), the provision of the output of music based on an onboard stored MP3 file, etc. Still further, in an exemplary embodiment, the body worn device 241 is further configured such that the functional suite automatically provides a second functionality when the chassis is removed from the body of the recipient. In an exemplary embodiment, the second functionality can be related to the hearing prostheses 100. It is noted that in some embodiments, this provision of the second functionality occurs in a seamless manner. In some embodiments, it occurs within 0.1, 0.5, 1, 1.5, 2, 2.5, 3, 4, or 5 seconds of a trigger event that triggers the activation of the second functionality. It is noted that in at least some exemplary embodiments, the body worn device is configured such that when the second functionality has been activated, the first functionality is deactivated or external indications of the first functionalities are paused. In this regard, by way of example only and not by way of limitation, in an exemplary embodiment where the body worn device 241 is to be utilized in conjunction with the hearing prosthesis, some or all other functionality of the body worn device is suspended or hidden during the period of time that the body worn device is so utilized. It is also noted that in some exemplary embodiments, the reverse is true as well: the second functionality of the body worn device is suspended, hidden, or terminated, while the body worn device is being worn. In a similar vein, it is noted that the aforementioned automatic switching to the second functionality can also be executed upon the occurrence of another trigger that corresponds to, for example, an action indicative of the recipient no longer desiring that the body worn device be utilized in conjunction with the hearing prosthesis. It is also noted that in some such embodiments, the aforementioned temporal periods can also be applicable as measured from the trigger to the implementation of the second functionality.

Some exemplary triggering events will now be described. By way of example only and not by way of limitation, in an exemplary embodiment, the body worn device 241, such as the aforementioned smartwatch, includes a sensor that is configured to provide input to the smartwatch indicating whether or not recipient is wearing the smartwatch on his or wrist or other location on the body. By way of example only and not by way of limitation, the sensor can be temperature-based, closed and/or open electrical circuit based (e.g., where skin tissue closes a circuit, or where the action of fastening one end of the band to the other end of the band closes a circuit), pressure based (e.g., a plunger type device can extend from the skin facing side of the watch, where the plunger is depressed upon the watch being attached to the rest of the recipient, the entire back surface of the watch can be spring-loaded and configured to move a short distance such that the pressure from the wrist pushes the back surface over a distance). In an exemplary embodiment, the watch can be configured to receive input from the recipient indicating whether or not the watch is being worn by the recipient. Any device, system, and/or method that can enable the watch to determine or otherwise receive input indicative of whether or not the watch as being worn on the recipient at a given time can be utilized in at least some exemplary embodiments.

Note also that in some exemplary embodiments, the smartwatch is configured to analyze the data from the sensor or the like and determine whether or not the smartwatch is being worn by the recipient at a given time. Alternatively, and/or in addition to this, owing to the fact that the smartwatch is in signal communication with the prostheses and/or owing to the fact that the smart phone is in signal communication with the smartwatch, in an exemplary embodiment, a signal can be provided from the smartwatch to the prostheses and/or to the smart phone, which signal can be indicative of whether or not the watch is being worn on the recipient, and the smart phone and/or the prosthesis can analyze said signal to determine whether or not the smartwatch is being worn on the recipient at a given time.

Figure 4:
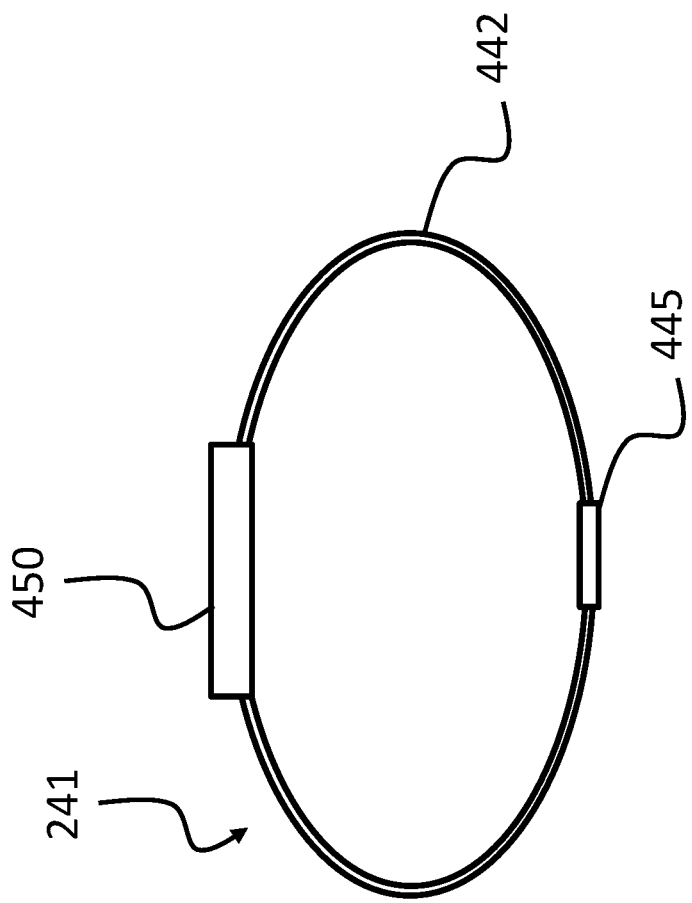
FIGS. 4 and 5 present exemplary embodiments of a smartwatch.
Figure 5:
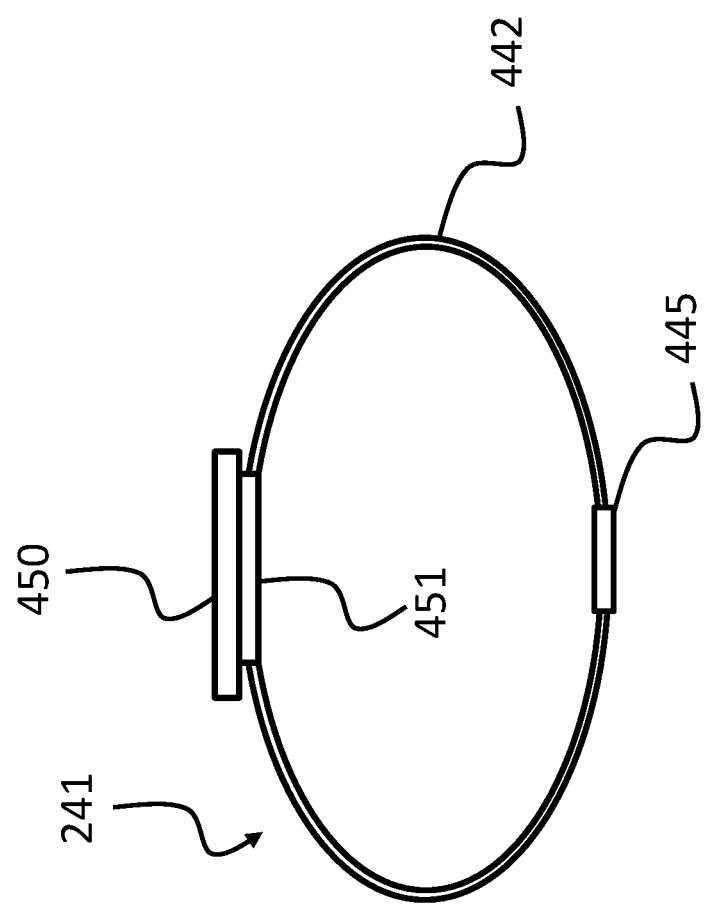

FIG. 4 depicts an exemplary schematic of a side view of a smartwatch 241 according to an exemplary embodiment. Here, band 442 is in the form of a wristband, the ends of which at the top are secured to the chassis 450 via a loop structure of the bands that extends through logs on either side of the chassis 450, and the ends of which at the bottom are held relative to one another via clasp 445. In this embodiment, the only normal way of removing the smartwatch 241 from the wrist of the wearer is to undo the clasp and remove the watch in a traditional manner. Conversely, FIG. 5 presents an alternate embodiment of a smartwatch 241, where the chassis 450 is removably connected to a chassis support 451 (which can also be a chassis, such as a frame or plate that supports the chassis 450). In an exemplary embodiment, the recipient can remove the chassis 450 from the chassis support 451 without removing the band 442 from the wearer's wrist. By way of example only and not by way of limitation, the chassis 450 can be mounted to the chassis support 451 via a quarter turn device, where the recipient turns the chassis 450 about 90° in a clockwise or counterclockwise direction relative to the band 442 and thus the chassis support 451, which turning on couples the chassis 450 from the chassis support 451, permitting the chassis to be removed from the recipient. In an exemplary embodiment, a magnetic coupling is present holding the chassis 450 to the chassis support 451, which magnetic coupling can be broken upon a sufficient force applied to the chassis, which force can be applied via the recipient's fingertips, etc. It is noted that in an exemplary embodiment, any or all of the aforementioned devices, systems, and/or methods that enable the generation of a signal indicative of whether or not the watch is being worn on the recipient are also applicable to the chassis 450. That is, in an exemplary embodiment, the watch 241 includes a sensor that is configured to output a signal indicative of whether or not the chassis 450 is connected to the chassis support 451. In an exemplary embodiment, the watch 241 and/or any of the other devices detailed herein can analyze the signal and determine whether or not the chassis 450 is connected to the chassis support 451. Is also noted that the two embodiments are not mutually exclusive. In this regard, in an exemplary embodiment there are sensors, the output of which can be utilized to determine whether or not the chassis support 451 is being worn on the recipient as well as sensors the output of which can be utilized to determine whether or not the chassis 450 is connected to the chassis support 451.

In an exemplary embodiment, the chassis and other supporting components are configured to enable a person other than the original wearer of the chassis to connect the chassis to a mating component worn by that other person, or otherwise enable the chassis to be worn by that other person. Indeed, in an exemplary embodiment, there is a method where the recipient removes the chassis/halts the chassis from being worn on his or her body, such as by removing the chassis of the smartwatch from the wristband, and provides the chassis to the person to whom he or she is speaking, whereby that person, or the original wearer, for that matter, in an alternate embodiment, places the chassis onto his or her body. In an exemplary embodiment, this action results in the chassis being worn on the other person's body. By way of example only and not by way of limitation, the chassis can support ancillary components, such as by way of example, a clip, that can enable the chassis to be clipped to another person's shirt pocket or the like. Still further by way of example and not by way of limitation, the original wearer of the chassis can also carry a separate chassis support assembly that is configured to be coupled to the chassis when the recipient intends for another person to wear the chassis. The recipient can place the chassis on to this chassis support assembly, and then provide the chassis now with the support assembly attached thereto to the other person. The chassis support assembly can include a clip or the like. In this way, the chassis support assembly is a completely separate component that is, in some embodiments, only used when the recipient seeks another person to wear the chassis. In an exemplary embodiment, the chassis support is a flat plate that includes resilient clips at edges thereof that envelope the sides and a portion of the top of the chassis to grip the chassis, and/or magnet(s), all that enable the removable attachment of the chassis support assembly to the chassis. Note also that in some exemplary embodiments, the chassis support assembly can be a component that is not a component that is worn. That is, the component is a non-wearable component. For example, it can instead be a device that supports the chassis in a certain orientation when the chassis is away from a human. The chassis support assembly can include legs that fold out so that the chassis is positioned at a desired angle. The legs can be adjustable. That said, in at least some exemplary embodiments, the chassis is worn in a manner analogous to or otherwise the same as how a remote mic for a hearing prostheses would be worn, where such remote mics are specifically designed to be carried by a speaker in some form or another to aid sound capture during the conversation.

In some embodiments, the aforementioned functionality where the device is configured such that the functional suite of the smartwatch or other body worn device automatically provides the second functionality when the chassis is removed from the body of the recipient corresponds to the removal of the chassis 450 from the chassis support 451, which removal will be interpreted as removal from the body of the recipient. It is noted that in at least some exemplary embodiments, even if the chassis support 451 is not being worn on the body of the recipient, the action of removal of the chassis from the chassis support 451 will be interpreted as the chassis being removed from the body of the recipient. In other embodiments, such will not be the case unless there is an affirmative baseline indicating that the chassis support 451 is being worn on the recipient (e.g., via input from the recipient through, for example, the touchscreen of the chassis 450, one or more of the aforementioned sensors, etc.).

In an exemplary embodiment, the second functionality is a remote microphone functionality of the hearing prosthesis. The body worn device is configured to communicate a signal indicative of a captured sound captured by the body worn device to the hearing prosthesis. By way of example only and not by way of limitation, in an exemplary embodiment, the microphone 251 can capture an ambient sound, and transduce that sound into a signal that is provided either directly or indirectly to a transmitter of the chassis of the smartwatch 241, which then transmits the signal or a signal based on the signal to the prostheses 100, which prosthesis 100 receives that signal and utilizes that signal to evoke a hearing percept based on that signal. In an exemplary embodiment, the smartwatch functions as a remote microphone of the prostheses 100. In an exemplary embodiment, the smartwatch 241 includes a sensor, such as one of the sensors detailed above, that outputs a signal upon the removal of the chassis from the wrist of the recipient. That signal is analyzed automatically by the smartwatch and/or by the prosthesis or another device, such as the smart phone 240. Upon a result of the analysis indicating that the chassis has been removed from the rest of the recipient, the second functionality is automatically engaged. In this exemplary embodiment, the second functionality is a streaming signal via link 230 from the chassis to the prosthesis 100, which streaming signal is based upon sound captured by the microphone 251.

In an exemplary embodiment, the chassis supports sensors therein or thereon that are configured to determine that the chassis is being worn by a person other than the recipient (in some other embodiments, other components of the prosthesis and/or the smart phone and/or another component, such as a smart phone or other device of the another person, are utilized to determine such). Alternatively and/or in addition to this, the onboard components are configured to make an assumption that the absence of a certain input corresponds to the chassis being worn by another person. By way of example only and not by way of limitation, in a situation where accelerometers or the like that are present in the chassis indicate frequent movements, but there is no signal from a sensor that is configured to indicate that the chassis is connected to the wristband, such will result in the determination that the chassis is being worn by someone else. Alternatively and/or in addition to this, the chassis can include a biometric analysis system that can evaluate one or more biometric parameters of a given wearer and/or person proximate to the chassis and determine whether or not the person is the original wearer, and if not, deduce that the person wearing the chassis is someone other than the original wearer.

Briefly, it is noted that while the embodiments detailed herein have focused upon the utilization of a smartwatch as the body worn device, in an alternative embodiment, the body worn device can be a pendant or the like or a finger ring. By way of example only and not by way of limitation, in an exemplary embodiment, the chassis 450 can be worn on a chain that extends about the neck of the recipient. In this regard, the chassis 450 may not be a chassis of a smartwatch, but in an alternative embodiment, the chassis of a piece of jewelry. By way of example only and not by way of limitation, the chassis can be made out of 24 karat gold and studded with seventeen diamonds of 0.25 karats each. The first functionality of this device can be an LCD screen that displays pictures of the wearers loved ones, and the second functionality can be the activation of the microphone supported by that 24 karat gold chassis. In an exemplary embodiment, the sensor can output a signal indicative of whether or not the chassis is against the skin of the recipient and/or can output a signal indicative of whether or not the chassis is connected to the aforementioned chain in a manner analogous to that detailed above vis-à-vis the interplay between chassis support 451 and chassis 450.

In is further noted that clothing provides protection from hot and cold conditions, safety during dangerous activities, a barrier between the wearer and rough surfaces, rash-causing plants, insect bites, unhygienic, infectious and toxic materials, and protection from the sun among other functions. Clothing also enables the wearer to conform to social and cultural norms and express personal taste or style. In at least some embodiment, body worn devices detailed herein are readily distinguishable from clothing. In such embodiments, the body worn devices detailed herein provide none of these functions primarily or secondarily. In such embodiments, for instance, the wristband 442 or other structure serves primarily or exclusively to support the chassis 450. Further, clothing is typically changed or removed depending on the activities of the wearer. The body worn devices detailed herein, in some embodiments, are configured to remain worn by the recipient while changing clothing or wearing no or minimal clothing (e.g., while bathing, swimming, sleeping, etc.). Indeed, in such embodiments, the body worn devices are not dependent on, attached to, or embedded in clothing and thus theoretically available to the wearer at all times.

It is noted that while the embodiments detailed herein have been described in terms of a sensor outputting a signal indicative of whether or not the chassis is being worn on the recipient and determining whether or not the chassis is being worn on the recipient based on that signal, it is noted that any such disclosure herein also corresponds to a disclosure where the sensor outputs a signal indicative of only that the chassis is being worn on the recipient and/or only that the chassis is not being worn on the recipient, and only determining based on the signal that the chassis is being worn on the recipient and/or only determining based on the signal that the chassis is not being worn on the recipient. That is, only one of the two binary situations are determined in some embodiments. That said, in some embodiments, both of the binary situations are determined. Any determination regime that can enable the teachings detailed herein can be utilized in at least some exemplary embodiments.

Figure 6:
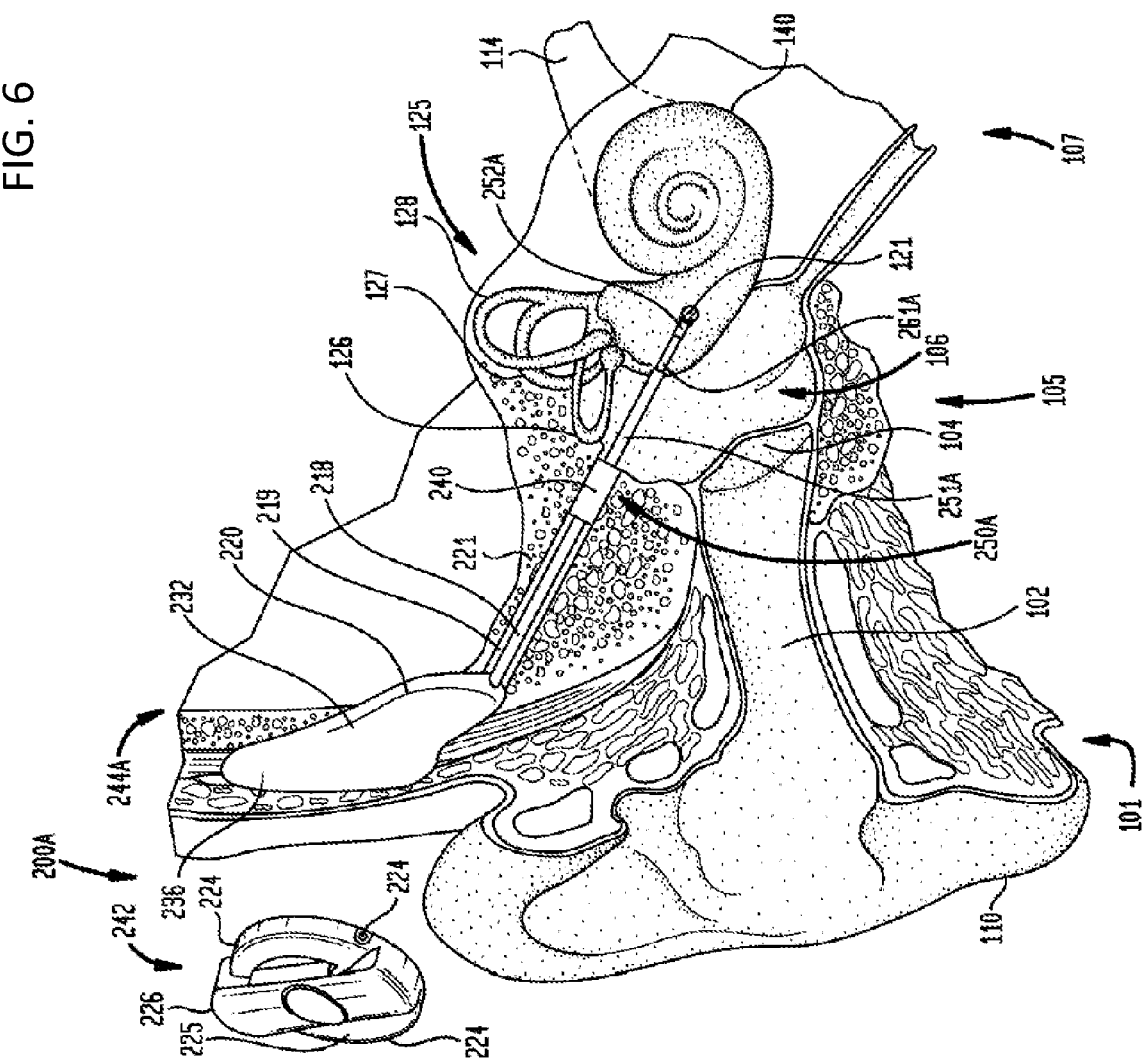
FIG. 6 is a perspective view of another exemplary hearing prosthesis in which at least some of the teachings detailed herein are applicable.

In an exemplary embodiment, the chassis 450 of the smartwatch or other body worn component can support or otherwise contain components that have a second functionality corresponding to that of an Off-The-Ear (OTE) sound processor of the prosthesis, which is retained against the skin of the recipient between the 9 and 12 o'clock position from the ear canal (e.g., about at the 10, 10:30 or 11 o'clock position more than 2 and less than 5 inches away therefrom in a human that is older than 10 years old meeting at least the $50^{th}$ percentile of such a human. Hereinafter, the term chassis 450 will be utilized as shorthand to refer to the chassis and the components supported thereby unless otherwise noted. More particularly, FIG. 6 is a perspective view of an exemplary direct acoustic cochlear stimulator 200A, which is another exemplary embodiment of hearing prosthesis 100. In this exemplary embodiment, the external component can be substituted by the chassis 450 from the smartwatch, as will be described. The embodiment where the chassis 450 can function as the external component/OTE sound processor will be described in terms of the direct acoustic cochlear stimulator 200A, although it is to be understood that in some alternate embodiments, the chassis 450 can function as the OTE sound processor of an active transcutaneous bone conduction device or a cochlear implant or another type of hearing prostheses, or another type of prosthesis in general. Indeed, in an exemplary embodiment, the implantable component is such that 232 and 220 are connected by electrical leads to an actuator (piezoelectric, electromagnetic actuator, etc.) that is configured to receive electrical signals from element 220 and vibrate based thereupon. Note also that in some exemplary embodiments, the actuator is in element 220 instead of being a separate module connected by electric leads. Conversely, the implantable component can correspond to the implantable components of FIG. 1.

Still, the following embodiment will be described in terms of utilizing the chassis as the OTE sound processor for the direct acoustic cochlear stimulator. First, some features of the stimulator 200A will now be described.

Direct acoustic cochlear stimulator 200A (in some embodiments, 200A can instead be a middle ear implant as modified appropriately to be such) comprises an external component 242 that is directly or indirectly attached to the body of the recipient, and an internal component 244A that is temporarily or permanently implanted in the recipient. External component 242, which here is in the form of an OTE sound processor, typically comprises two or more sound input elements, such as microphones 224, for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient. Internal component 244A comprises an internal receiver unit 232 to which is attached an inductance coil 236 section having an inductance coil therein, a stimulator unit 220, and a stimulation arrangement 250A in electrical communication with stimulator unit 220 via cable 218 extending through artificial passageway 219 in mastoid bone 221. Internal receiver unit 232 and stimulator unit 220 are hermetically sealed within a biocompatible housing, and are sometimes collectively referred to as a stimulator/receiver unit.

Internal receiver unit 232 comprises an internal coil (not shown), and optionally, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable receiver unit 232 is positioned in a recess of the temporal bone adjacent auricle 110.

In the illustrative embodiment of FIG. 6, ossicles 106 have been removed or otherwise are not present. However, it should be appreciated that stimulation arrangement 250A may be implanted without disturbing ossicles 106.

Stimulation arrangement 250A comprises an actuator 240, a stapes prosthesis 252A, and a coupling element 251A which includes an artificial incus 261A. Actuator 240 is osseointegrated to mastoid bone 221, or more particularly, to the interior of artificial passageway 219 formed in mastoid bone 221.

In this embodiment, stimulation arrangement 250A is implanted and/or configured such that a portion of stapes prosthesis 252A abuts an opening in one of the semicircular canals 125. For example, in the illustrative embodiment, stapes prosthesis 252A abuts an opening in horizontal semicircular canal 126. In alternative embodiments, stimulation arrangement 250A is implanted such that stapes prosthesis 252A abuts an opening in posterior semicircular canal 127 or superior semicircular canal 128.

As noted above, a sound signal is received by microphone(s) 224, processed by sound processing unit 226, and transmitted as encoded data signals to internal receiver 232. Based on these received signals, stimulator unit 220 generates drive signals which cause actuation of actuator 240. The mechanical motion of actuator 240 is transferred to stapes prosthesis 252A such that a wave of fluid motion is generated in horizontal semicircular canal 126. Because vestibule 129 provides fluid communication between the semicircular canals 125 and the median canal, the wave of fluid motion continues into the median canal, thereby activating the hair cells of the organ of Corti. Activation of the hair cells causes appropriate nerve impulses to be generated and transferred through the spiral ganglion cells (not shown) and auditory nerve 114 to cause a hearing percept in the brain.

Figure 7:
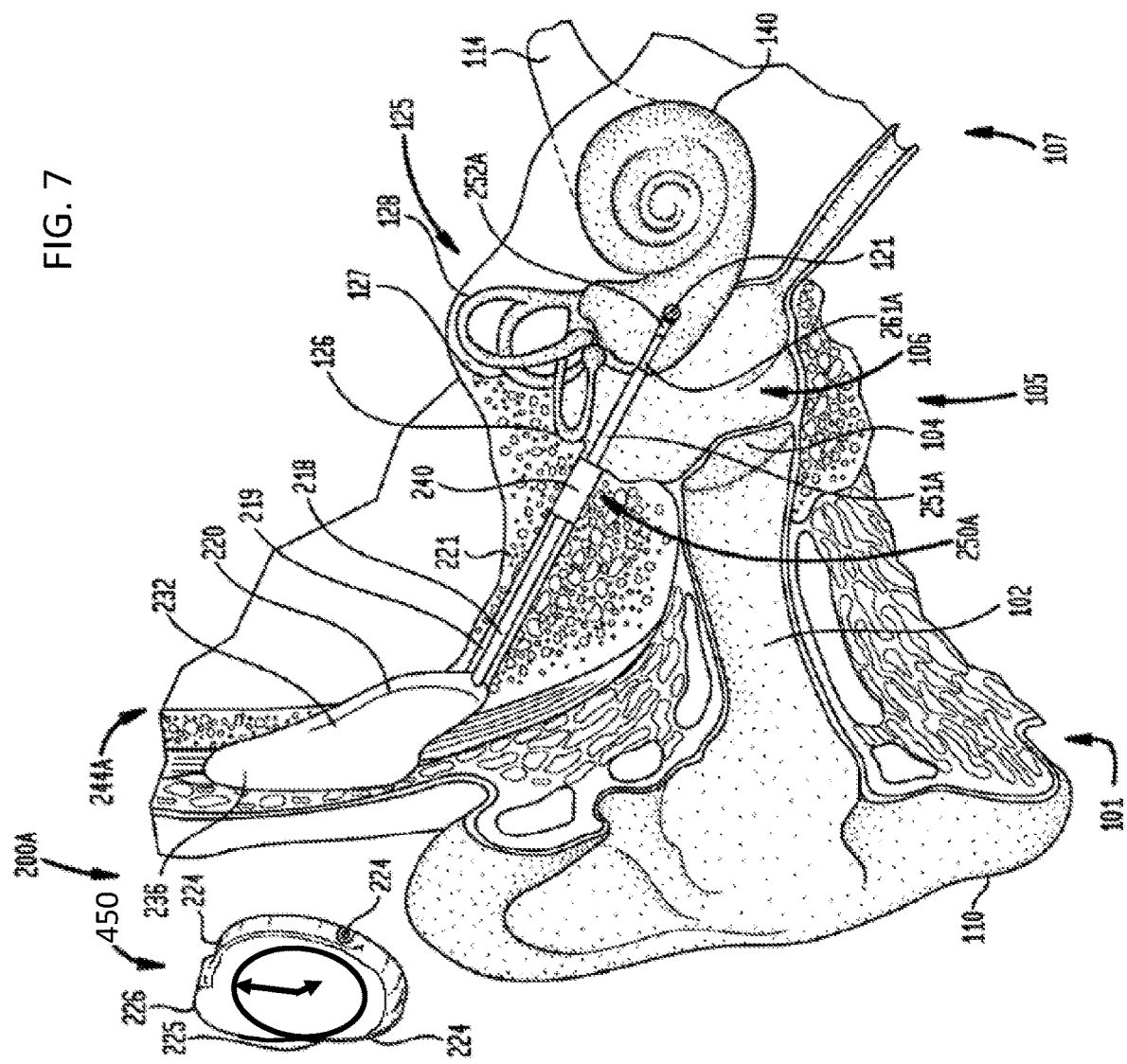
FIG. 7 is a perspective view of the exemplary hearing prosthesis of FIG. 6 according to an exemplary embodiment.

FIG. 7 depicts the direct acoustic cochlear stimulator 200A in a scenario where the chassis 450 from the smart watch 241 is utilized as the OTE sound processor. In this regard, in an exemplary embodiment, the chassis 450 contains one or more or all of the aforementioned components of the external component 242. In an exemplary embodiment, the chassis 450 is removed from the chassis support 451 and then placed against the head of the recipient above the implanted inductance coil section 236. In an exemplary embodiment, the chassis 450 contains a magnet that interfaces with the magnetic field generated by the implantable magnet to align and otherwise hold the chassis 450 against the skin of the recipient. That said, in an alternate embodiment, there is no magnet in the chassis 450 or otherwise that is a part of the chassis 450. Instead, the recipient may just simply hold the chassis 450 against his or her head to use the chassis 450 as the OTE sound processor (the chassis 450 and the components supported thereby as the OTE sound processor).

Accordingly, in an exemplary embodiment, the second functionality of the wearable device is a functionality of an OTE sound processor, and at least one of the chassis or a component supported by the chassis is a ferromagnetic material such that the chassis can be held against skin of the recipient via an implanted magnet implanted in the recipient. In this regard, in some embodiments, the chassis can contain a magnet and/or the chassis can be made of magnetic material. In some embodiments, the chassis is simply a ferromagnetic material that is not a permanent magnet or the like and/or the chassis simply contains a ferromagnetic material that is not a permanent magnet, where in this embodiment, the chassis 450 relies on the implanted magnet to generate the magnetic field.

In view of the above, it can be understood that in at least some exemplary embodiments, the body worn device of at least some exemplary embodiments is configured to wirelessly communicate with an implanted component of the recipient. This can be the case whether or not the body worn device has a functionality as an OTE sound processor. That said, it is also noted that in at least some exemplary embodiments, irrespective of whether or not the smart watch or otherwise the body worn device has the functionality of an OTE sound processor, in at least some exemplary embodiments, the body worn device has at least one or more of the components and/or functionalities of the external component 242 described above.

It is noted that the embodiments described above have been presented in terms of the second functionality being enabled in an automatic manner. In some exemplary embodiments of such an exemplary embodiment, the body worn device is configured to automatically prompt a wearer for input as to whether the second functionality is desired. In this regard, in an exemplary embodiment, the wearer has the ability to override the activation or otherwise the enablement of the second functionality. By way of example only and not by way of limitation, in an exemplary embodiment, the LCD screen supported by the chassis 450 can display a message in text to the recipient that the body worn device will execute the second functionality within five seconds, and a timer timing down those five seconds can be shown on the display. If the recipient taps the screen twice or, for example, makes an X in the screen with his or her finger, etc., or touches a button on the side of the chassis or the like, or otherwise provides input into the body worn device that the second functionality is not desired, the second functionality activation is belayed or otherwise not prevented to be engaged. The prompt can also be an audible prompt or a tactile prompt. Indeed, in an exemplary embodiment, the prompt can be a signal to the prosthesis that enables the prosthesis to evoke a hearing percept, which could potentially be preprogrammed into the hearing prosthesis, that the second functionality is going to be enabled unless the recipient does something.

Any device, system, and/or method that can enable the body worn device to prompt the wearer for input as to whether the second functionality is desired can be utilized in an exemplary embodiment.

It is briefly noted that while the embodiments detailed herein have generally focused on the utilization of a inductance coil being present in the chassis 450 or otherwise supported on the chassis 450, so as to provide inductance communication with the implantable component, in some other embodiments, any other regime of communication with the implantable component can be utilized, such as by way of example only and not by way of limitation, a Bluetooth system or other low-energy communication regimes. It is briefly noted that while some embodiments utilize the external component to power the implantable component via transcutaneous inductance transfer from the external component (e.g., the OTE sound processor or the BTE device, etc.), in some other embodiments, the implantable component is configured to operate without power transfer from the external component, at least for a limited period of time. In this regard, in some exemplary embodiments, when the body worn device is utilized as, for example, an OTE sound processor, or otherwise as the external component of the prosthesis, in an exemplary embodiment, the body worn device does not need to power the implantable component. By way of example only and not by way of limitation, in some exemplary embodiments, the implantable component includes a battery or the like that can power the implantable component. Indeed, such can be the case with respect to a totally implantable device.

It is also noted that while the embodiment described above focuses on direct contact between the chassis of the body worn device and the skin of the recipient, in an alternate embodiment, contact between the skin and the chassis of the body worn device does not necessarily occur for the body worn device to be utilized as part of a prosthesis. Note also that in at least some exemplary embodiments, there is no magnet or the like in or otherwise supported by the chassis. In this regard, in an exemplary embodiment, there is no need for physical attachment of the chassis to the recipient (again, in some embodiments, the recipient can also simply hold the chassis adjacent the implanted component for the period of time utilized with the prosthesis).

Accordingly, in an exemplary embodiment, there is a multiuse device, comprising a housing, such as in embodiments where the chassis 450 is a housing (which can be mutually exclusive in some embodiments, while in other embodiments a chassis can be the housing), and a wristband 442 or other looped structure (e.g., necklace, arm band—more on this below). In this exemplary embodiment, an operating system is supported by the housing. By way of example only and not by way of limitation, the operating system can be a miniaturized computer or can be a smartwatch system, and/or can include RF communication features and/or can include mobile telephone/videophone capabilities. In an embodiment where the multiuse device is a smartwatch, the smartwatch is thus configured to be worn on a wrist of a recipient of a hearing prosthesis and secured thereto by the wristband. In this particularly refined embodiment, the multiuse device is configured to interact with a hearing prosthesis, such as any of the hearing prostheses detailed herein. In an exemplary embodiment, the multiuse device is configured to interact with the BTE device of the hearing prosthesis and/or with the OTE sound processor of the hearing prosthesis and/or whatever applicable external component is utilized there with. In an exemplary embodiment, the multiuse device configured to interact with the implantable component(s) of the hearing prosthesis. Indeed, in this exemplary embodiment, the housing is removable from the wristband and can be placed against the skin of the recipient such as the skin over the mastoid bone/the skin over the implantable component such as over element 236 (the coil). In this regard, the housing can correspond to element 450 of FIG. 7 (it is noted while the embodiment of FIG. 7 discloses a housing that is generally circular in shape, in an exemplary embodiment, the housing can be rectangular shaped, oval shaped, etc.).

Consistent with the teachings detailed above, in an exemplary embodiment, the multiuse device is configured such that the housing is operationally releasable from the wristband, and the housing is configured to be held against skin of a recipient via a magnetic field generated by at least one of an implanted magnet or a magnet supported by the housing.

In some embodiments, the multiuse device is configured to receive input from the recipient and control the hearing prosthesis based on the input. In this regard, the housing can support buttons or otherwise touch sensitive features (e.g., a touch sensitive screen) that enable the recipient to activate a given functionality of the hearing prosthesis by providing input thereby (the touch sensitive features), where the multiuse device analyzes the input and/or passes along the input to the hearing prostheses via an RF signal. Alternatively, and/or in addition to this, some embodiments of the multiuse device are configured to receive audio commands from the recipient. By way of example only and not by way of limitation, the hearing prosthesis and/or the multiuse device can be configured to recognize verbal commands from the recipient that indicates activation of a functionality of the hearing prosthesis. For example, a recipient can speak "prosthesis, enable noise cancellation." These words, or words similar thereto, would activate the functionality associated with noise cancellation. The recipient would then speak the desired type of noise cancellation, and the sound of the recipient's speech would be captured by the microphones or other appropriate device on the housing/supported by the housing.

Note also that the received input can be in the form of an adjustment to an existing functionality that is already operating on the prosthesis. By way of example only and not by way of limitation, such can be utilized to adjust the volume and/or the gain setting of the prosthesis.

In some embodiments, the aforementioned multiuse device is configured to provide backup functionality to the hearing prosthesis, such as in the event of a failure of a component, or due to battery power levels, etc. In some embodiments, the aforementioned multiuse device is configured to provide supplemental functionality to the hearing prosthesis, such as in the case where the features of the multiuse device simply provide better results, even though the underlying functionality that is supplemented is still available if, for example, the recipient wanted to use such (by way example and not by limitation, such as where the prosthesis is a totally implantable device, and an external microphone captures sound better than the implanted microphone). Any disclosure herein of backup functionality corresponds to a disclosure of supplemental functionality, and visa-versa. Indeed, the aforementioned backup/supplemental functionality is consistent with the above, where the chassis/housing 450 of the smartwatch can be utilized as the OTE sound processor by putting such against the skin of the recipient as shown in FIG. 7. Still further, in an exemplary embodiment, the multiuse device provides the ability to adjust features of the hearing prosthesis, such as volume or the like. The idea here is that in some embodiments, the multiuse device is a stand-in for another component of the hearing prosthesis, where the absence of such another component will prevent the hearing prosthesis from operating properly. Thus, in an exemplary embodiment, there is a device according to that described above and/or below, wherein the multiuse device is a back-up sound processor for the hearing prosthesis.

In an alternate embodiment, the multiuse device is configured to operate as a wireless accessory to the hearing prosthesis, such as, by way of example, a remote microphone. In an exemplary embodiment of this exemplary embodiment, the housing/chassis 450 of the smartwatch can be removed from the band and placed on a table or the like or even handed to a speaker speaking to the hearing impaired person so that the speaker can hold the housing/chassis closer to his or her mouth so as to more easily capture sound emanating therefrom or otherwise can be simply placed at a location that is more conducive to capturing sound relative to that which is the case with respect to the strictly dedicated components of the hearing prosthesis. In this exemplary embodiment, the microphone(s) supported by the housing/chassis capture the sound of the speakers voice or whatever sound source is desired to be captured, and the speakers transduce the captured sound into an electrical signal which is either processed or unprocessed and then the multiuse device generates an RF signal based on the captured sound, which signal is sent to the hearing prostheses (e.g., to an RF receiver of the BTE device or the OTE sound processor or other external component), whereupon the hearing prosthesis utilizes the received signal to evoke a hearing percept.

In some embodiments, the multiuse device as described above and/or below communicates with the hearing prosthesis utilizing non-inductance communication. In this regard, in an exemplary embodiment, Bluetooth technology can be utilized. In an exemplary embodiment, any RF signal regime that can enable the teachings detailed herein can be utilized. In an exemplary embodiment of the embodiment that utilizes non-inductance communication, the chassis/housing 450 can include an RF transmitter and the external component of a hearing prostheses, such as the BTE device or the OTE sound processor, can include an RF receiver that receives the signal generated by the RF transmitter. Note further that in some embodiments, the implanted prosthesis can include an implanted antenna in the recipient, which implanted antenna receives the non-inductance signals.

Figure 8:
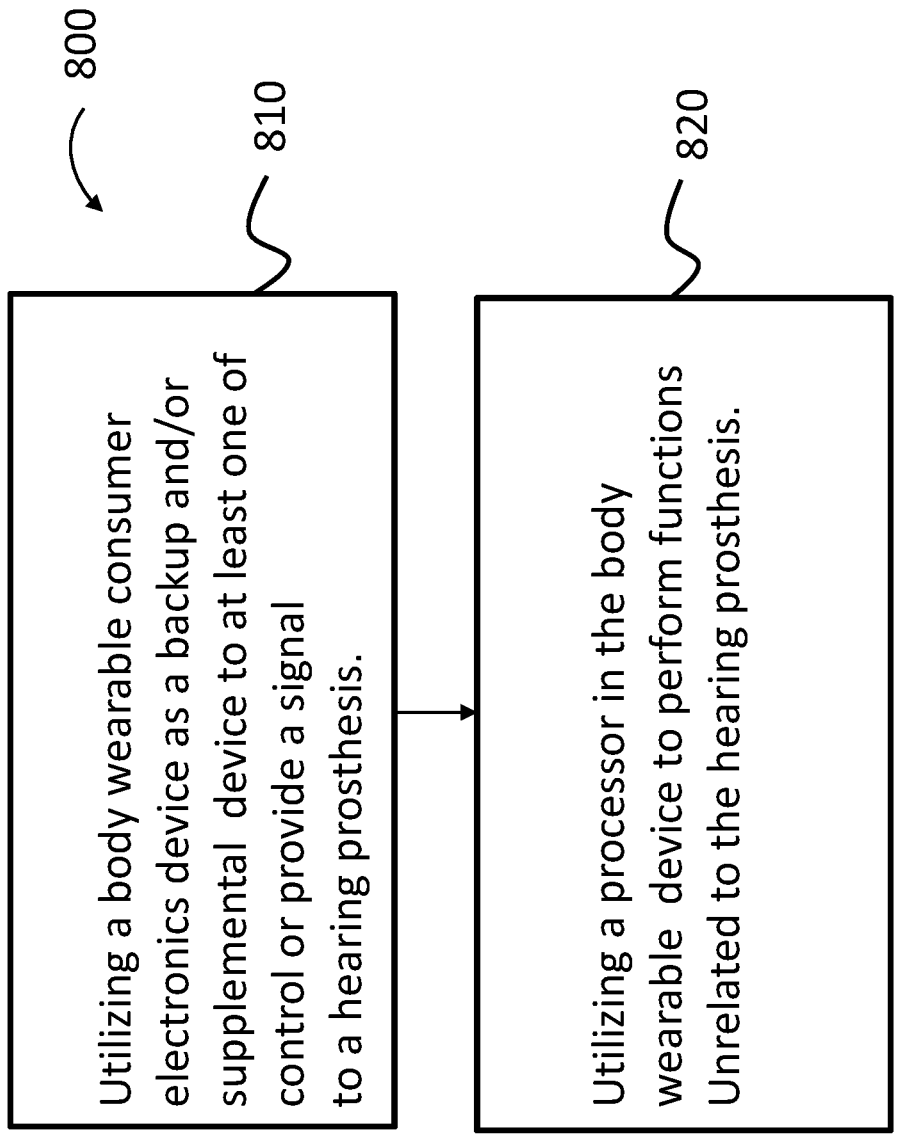
FIGS. 8 and 9 present exemplary flowcharts for exemplary methods according to exemplary embodiments.

FIG. 8 presents an exemplary flowchart for an exemplary method, method 800. Method 800 includes method action 810, which includes utilizing a body wearable consumer electronics device as a backup device and/or a supplemental device to at least one of control or provide a signal to a hearing prosthesis. With respect to the latter, as detailed above, in an exemplary embodiment, the body wearable consumer electronics device, such as that in the form of a smartwatch, is configured to provide an RF signal that is based upon captured sound captured by the microphones of the smartwatch. With respect to the former, in an exemplary embodiment, as noted above, the recipient can input control input into the smartwatch so as to adjust a volume or a gain or activate or deactivate a noise control system or otherwise adjust the noise control system or, in an exemplary embodiment activate and/or adjust a beamforming system of the prostheses. Method 800 further includes method action 820, which includes utilizing a processor in the body wearable device to perform functions unrelated to the hearing prosthesis. By way of example only and not by way of limitation, functions unrelated to the hearing prosthesis can be utilizing the body worn consumer electronics device, where the body worn device is a smartwatch, as a smartwatch. Still further, such can be executed while the smartwatch is worn on the wrist of the recipient. Still further, in an exemplary embodiment, the functions unrelated to the hearing prosthesis can be utilizing the body worn device to unlock a door, start a car, talk to someone that is not in the general vicinity of the recipient, make a cellular phone telephone call or receive a cellular phone telephone call, etc. It is noted that in at least some embodiments, the action of utilizing the processor in the body wearable device to do functions unrelated to the hearing prostheses can correspond to any of the actions that are enabled by the smart phone devices detailed above from Apple or Samsung that are commercially available in the United States of America, the State of California, or the Commonwealth of Virginia, as of Jul. 4, 2017.

In an exemplary embodiment, method action 820 is executed while using a primary body wearable device of the hearing prosthesis to at least one of control or provide a signal to the hearing prosthesis. In an exemplary embodiment, the primary body wearable device is a BTE or an OTE sound processor, etc., and the electronics device is different therefrom. In this regard, in an exemplary scenario, the recipient of the hearing prosthesis can utilize the hearing prosthesis in the ordinary and customary manner, such as where the external device is capturing sound utilizing a microphone thereof, and providing signals to the implanted component via the inductance coil system so that the implanted component can evoke a hearing percept based thereon. While this is going on, the recipient can also utilize the body wearable device in a manner concomitant with its ordinary and customary use, such as utilizing the body wearable device as a smartwatch. In an exemplary embodiment, the body wearable device is utilized as an interface with a smart phone which is in signal communication with the body wearable device. In an exemplary embodiment, the body wearable device utilizes a microphone that captures sound and generates an RF signal based on the captured sound, which is received by a smart phone, where the smart phone has a cellular phone system and the smart phone communicates with a cell tower. Still further, in an exemplary embodiment, the body wearable device includes an RF receiver that receives an RF signal from a smart phone having a cellular phone system, which signal is based on a received signal from a cell phone tower having voice data therein from someone with whom the recipient is speaking. The body wearable device receives the signal and outputs from the speaker of the body wearable device, such as a speaker supported by the housing/chassis 450, an audio signal corresponding to the voice of the person on the other end of the cell phone call.

In an exemplary embodiment, the recipient exchanges text messages utilizing the body worn device while utilizing the external component of the hearing prosthesis. In an exemplary embodiment, the body worn device is configured with a touchscreen that is in signal communication with a processor that displays an alphanumeric keyboard on the display a keyboard based on output from the processor, and is displaying text received from a person remote from the recipient, which text is communicated to the body worn device utilizing a cell phone system or utilizing a Bluetooth system, etc., while the recipient is using the external component in the hearing prosthesis to evoke a hearing percept. In an exemplary embodiment, the recipient inputs into the touchscreen input information to type text on the touchscreen and this text is sense via the cellular phone system or the Bluetooth system, etc. ultimately, to the person remote from the recipient, again while the external component is being utilized with the hearing prosthesis.

In an exemplary embodiment, method action 820 is executed at least once a day for a week before method action 810 is executed. In an exemplary embodiment, method action 820 is executed at least D times per day for P days before method action 810 is executed. In an exemplary embodiment, D is 1, 2, 3, 4, 5, 6, 7, 8, 9, 10 or more, and P is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 90, 120, 150, 200, 250, 300, 350, 400, 500 or 600 or more.

In an exemplary embodiment, consistent with the teachings detailed above, method action 810 is executed by utilizing the consumer electronics device as a remote mini microphone. Again, in an exemplary embodiment, this can include providing the chassis/housing of the smartwatch to a speaker so that the speaker can hold the smartwatch close to his or her mouth, and the smartwatch is in radiofrequency communication with the hearing prosthesis of the recipient, such that the smartwatch broadcasts a signal based on the captured sound from the speakers mouth to the hearing prostheses, whereupon the hearing prosthesis evokes a hearing percept based on the received signal. Alternatively, the recipient can place the chassis on a table or place the chassis on some other surface that can have utilitarian value with respect to capturing sound. Still further, in an exemplary embodiment, the recipient need not remove the chassis from the smartwatch. In an exemplary embodiment, the recipient can hold his or her wrist towards the "audio projectile" to better capture the sound.

In an exemplary embodiment, still consistent with the teachings detailed above, method action 810 is executed by utilizing the consumer electronics device when a component of the hearing prosthesis is functionally unavailable to at least partially achieve the functionality of the component. By way of example only and not by way of limitation, consider the scenario where, for example, the battery of the BTE device has no remaining charge, and thus the electronics of the BTE device cannot be powered. In an exemplary embodiment, the recipient can utilize the smartwatch as the sound capture device and/or as the sound processor, providing of course that the smartwatch has such functionality. By way of example only and not by way of limitation, in an exemplary embodiment, the recipient can remove the chassis from the wristband, and unplug the cable leading from the inductance coil of the external component to the BTE device, and plug the cable into the chassis so that the chassis will be in wired signal communication with the inductance coil of the external component. In this regard, it is to be understood that in an exemplary embodiment, the smartwatch or other body wearable consumer electronics device can have a port configured to receive or otherwise connect to the aforementioned cable. Still, consistent with some of the embodiments above, the smartwatch can communicate with the inductance coil the external component wirelessly in some embodiments. Alternatively, again as consistent with the teachings detailed above, in an exemplary embodiment, instead of utilizing the inductance coil of the external device, the recipient can utilize the inductance coil of the body wearable consumer electronics device to communicate with the implantable component by placing the chassis against his or her skin over the temporal bone as detailed above.

It is noted that in at least some exemplary embodiments, the smart phone can be configured to control the smartwatch and/or vice versa. In an exemplary embodiment, the smart phone can be configured to activate and/or deactivate the smartwatch, activate and/or deactivate a given feature of the smartwatch or otherwise a given functionality of the smartwatch (e.g., activate the microphone, deactivate the microphone, an audio processing routine, etc.) and/or visa-versa. In an exemplary embodiment, the aforementioned controls can be executed automatically and/or manually using the respective applicable devices. Indeed, in some exemplary embodiments, the smart phone can be utilized to control the smartwatch while the smartwatch (or chassis thereof) is being worn by a person other than the original wearer. All of this can also be the case with respect to the prosthesis as well. By way of example only and not by way of limitation, in an exemplary scenario where the chassis is being worn by another person, the recipient/original wearer can utilize the smart phone to adjust features of the microphone remotely and, in some instances, in a manner completely transparent to the other person. All of this can also be the case with respect to the prosthesis as well: the prosthesis can control and/or be controlled by the smartwatch and/or the smartphone, etc.

In an exemplary embodiment where the smartwatch has the functionality to control the prosthesis, the smartphone can be utilized as an alternate controller for the prosthesis when the smart watch is being utilized (such as, for example, where the smart watch is being utilized as a remote microphone, as an OTE device, etc.—by way of example and not by way of limitation, any of the second functionality detailed herein). Indeed, in an exemplary embodiment, upon activation of the smart watch second functionality detailed above, any control functionality of the smart watch can be migrated to the smart phone, in some instances, automatically, and in other instances, after the selection of a prompt that appears on the smart watch and/or smart phone. In an exemplary embodiment, upon removal of the smart watch or a portion thereof from the body of the recipient, the control functionality can be automatically migrate or migrated via the aforementioned prompt, for example (where, for example, the prompt can be automatically provided due to the removal). Thus, in an exemplary embodiment, the smart phone can be used as a control device while the smart watch is being used according to the second functionality thereof and/or while such is removed from the body.

As noted above, in some embodiments, the smart phone can be used to control the smart watch. In an exemplary embodiment of this embodiment, the smart phone can control the smart watch while the smart watch is being used according to the aforementioned second functionalities, such as, for example, as an OTE device. Such can have utilitarian value in a scenario where, for example, the recipient cannot see the smart watch as it is located on his or her head and outside his or her field of vision. The smart phone can be utilized to control first functionality and/or second functionality. For example, if a scenario exists where the recipient seeks to implement a noise cancellation routine in the sound processor, and the sound processor is the smart watch and the chassis thereof is magnetically coupled to the side of the recipient's head, the smart phone can be utilized to activate the noise cancellation routine of the sound processor of the smart watch, or adjust that routine, etc.

Note that this embodiment can be executed even if the hearing prosthesis utilizes a BTE device. In this regard, in at least some exemplary embodiments, the utilization of the consumer electronics device as an OTE sound processor is not mutually exclusive with utilization with a hearing prosthesis that also utilizes an OTE sound processor. Of course, consistent with the teachings detailed above, in an exemplary embodiment, the scenario that resulted in the utilization of the consumer electronics device as a backup device or a supplemental device can be a scenario where the OTE sound processor has ceased operation with respect to the former or simply is not providing as good performance or a desired performance as the consumer electronics device utilized with respect to the latter. Backup device utilization can be the case in an exemplary scenario where, for example, there exists the exhaustion of a battery of the OTE sound processor, or the OTE sound processor has been damaged, etc. Still further, in an exemplary scenario, the OTE sound processor and/or the BTE device of the recipient is simply not available. By way of example only and not by way of limitation, this can be a scenario where the recipient is swimming or taking a shower or the like, and the recipient is wearing his or her watch but is not wearing his or her BTE device or OTE sound processor. In this exemplary scenario, for whatever reason, the recipient is in immediate need of the functionality of the external component of a hearing prosthesis, and the body worn consumer electronics device is the closest device to the recipient that can provide such functionality.

Note also that in an exemplary embodiment, the body wearable consumer electronics device is utilized in a scenario where, for example, a remote mic is not immediately available to the recipient. Again, consider a scenario where, for example, the recipient is going to take a shower. In some exemplary embodiments, the recipient takes off his or her watch and places it on, for example, the sink or the like, so that the hearing prosthesis system can capture sound that is remote from the sound of running water, which will interfere or otherwise make it more difficult for the recipient to hear. In this exemplary embodiment, the recipient in fact could be taking a shower with an external component that is waterproof. That said, in an alternative embodiment, the recipient could have a totally implanted device that does not include an external component, and thus the body worn consumer electronics device is being utilized as the remote mic.

It is also noted that in at least some exemplary embodiments, the body worn consumer electronics device can be utilized as an emergency shutoff system for the implanted prosthesis. By way of example only and not by way of limitation, in an exemplary embodiment, the body worn device can have as its only additional functionality relative to the normal functionality not associated with a hearing prosthesis or other prosthesis, the ability to shut the implanted prostheses down (or, in some embodiments, to activate the prosthesis), nothing more. Of course, in some embodiments, this is in addition to the other functionalities associated with the hearing prostheses.

In an exemplary embodiment, method action 810 consists of utilizing the consumer electronics device when a component of the hearing prosthesis is functionally unavailable to at least partially achieve the functionality of the component.

It is noted that the method actions detailed herein have been presented in a sequence where one method action has been presented before the other. It is noted that in at least some exemplary embodiments, the sequences are different than that presented. To be clear, in an exemplary embodiment, any method action can be executed in any order relative to any other method action unless otherwise specified herein, providing that the art enables such.

Figure 9:
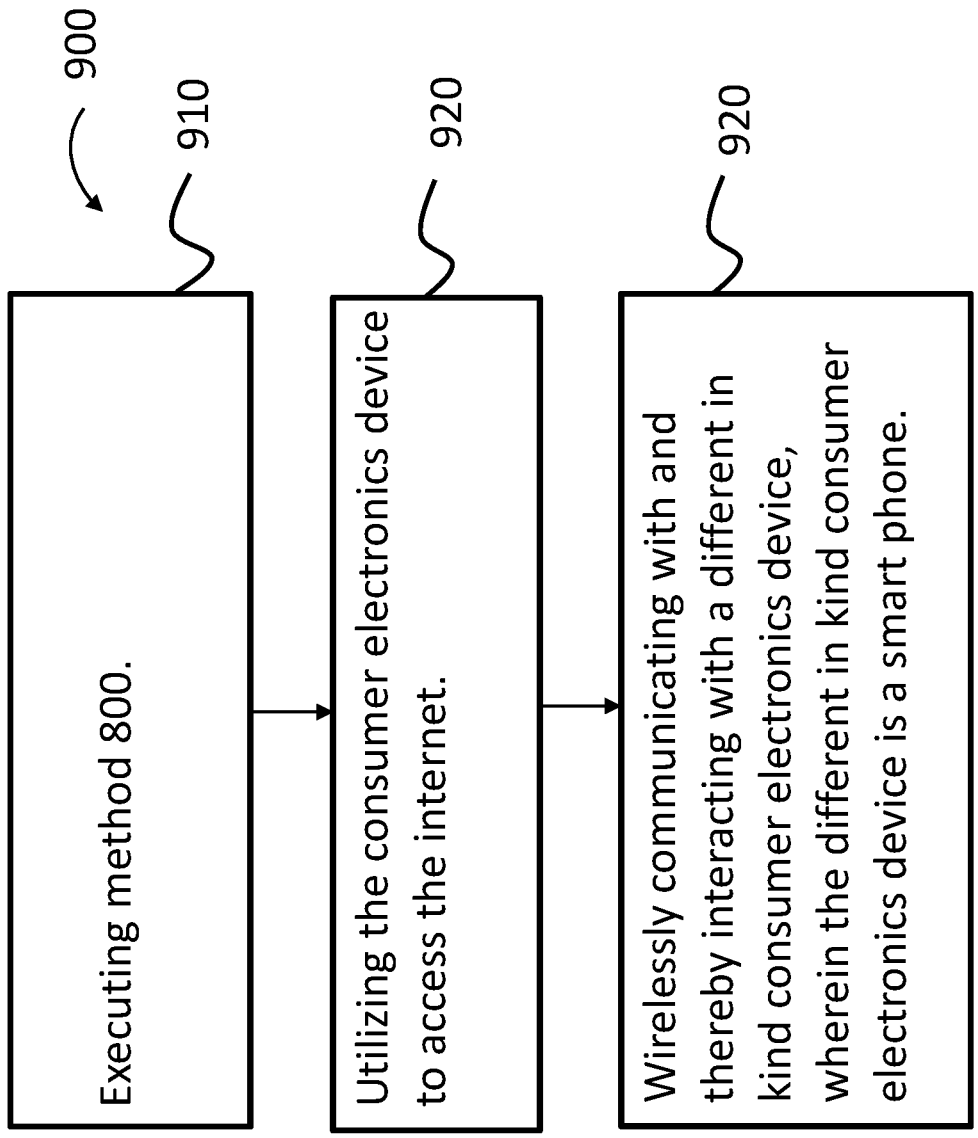

FIG. 9 presents an exemplary flowchart for an exemplary method, method 900, according to an exemplary embodiment. Method 900 includes method action 910, which includes executing method 800. Method 900 further includes method action 920, which includes utilizing the body wearable consumer electronics device to access the Internet. In this regard, by way of example only and not by way of limitation, the body wearable consumer electronics device can be a smartwatch, and the recipient can access the Internet by inputting data into the touchscreen and receiving data from the Internet there from, where the smartwatch is in signal communication via RF signal or via cellular system or Bluetooth, etc., either directly or indirectly (e.g., such as when the smartwatch is utilized as an interface with a smart phone) with a server.

Method 900 further includes method action 920, which includes wirelessly communicating with and thereby interacting with a different in kind consumer electronics device, wherein the different in kind consumer electronics device is a smart phone. In this regard, in this exemplary embodiment, the smart watch can be an interface between the recipient and a smart phone. In an exemplary embodiment of this method action, the recipient utilizes the smartwatch to capture the sound of the recipient's voice, and the smartwatch transmits a signal to the smart phone based on the recipient's voice and/or the smart phone transmits a signal having audio content therein to the smartwatch, and the smartwatch produces an audio sound utilizing speakers thereof, where, in this exemplary embodiment, the audio sound is the sound of someone remote from the recipient with whom the recipient is speaking.

It is noted that any method action detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by a human being. It is further noted that any disclosure of a device and/or system detailed herein corresponds to a method of making and/or using that the device and/or system, including a method of using that device according to the functionality detailed herein.

It is noted that embodiments include non-transitory computer-readable media having recorded thereon, a computer program for executing one or more or any of the method actions detailed herein. Indeed, in an exemplary embodiment, there is a non-transitory computer-readable media having recorded thereon, a computer program for executing at least a portion of any method action detailed herein.

In view of the above, it can be seen that in some exemplary embodiments, there is a multiuse device, comprising a housing, such as a housing established by chassis 450, and an operating system supported by the housing, which operating system can be any of those detailed herein or variations thereof. In an exemplary embodiment, the multiuse device is configured to enable the housing to be supported by a human body at two different types of body parts (e.g., head, neck, wrist, finger, etc.). Consistent with the teachings detailed above, in an exemplary embodiment, the housing can be supported via a wristband, and thus be supported on the wrist of the recipient, and can also be supported via a magnetic coupling through skin of the recipient at a location off the ear of the recipient, such as over the mastoid bone. Consistent with the teachings detailed above, the multiuse device is configured to interact with a hearing prosthesis supported by a human body.

In an exemplary embodiment, the multiuse device includes a first body support apparatus configured to support the housing at a first type of body part. By way of example only and not by way of limitation, this can correspond to a wristband or an armband or a ring or a neck chain. Still further, in an exemplary embodiment, the housing is configured with a second body support apparatus configured to support the housing at a second type of body part without the first body support apparatus. By way of example only and not by way of limitation, the housing that supports or otherwise is attached to a ferromagnetic material that will interact with an implanted magnet can enable such configuration. That is, the housing can be configured to be retained against skin of the human via a magnetic field generated by an implanted magnet in the human body that interfaces with the ferromagnetic material to establish attraction therebetween.

In some embodiments, the body support apparatus is a device that is easily removed from the body and/or easily repositioned on the body. Such can have utilitarian value with respect to providing a readily available device for implementation of the aforementioned second functionalities detailed above and/or where the functionality desired of the body worn device requires that the device not be worn on the recipient while that functionality is being utilized. Further, in some embodiments, the aforementioned chassis is a device that is easily removed from the body support and/or easily repositioned on/reattached to the body support.

In an exemplary embodiment, the devices are configured such that the aforementioned removal and/or reattachment/repositioned actions can be respectively executed in less than 0.5, 0.75, 1, 1.5, 2, 2.5, 3, 3.5, 4, 4.5, 5, 5.5, 6, 6.5, or 7 seconds by a 50 percentile human factors male or female citizen of the United States of America as of Jul. 4, 2017.

Consistent with the teachings detailed above, in at least some exemplary embodiments, the housing is releasably supported by the first body support apparatus. For example, in the embodiment where the first body support apparatus is a wristband, the housing can be releasably supported thereby in accordance with the teachings detailed above, for example. Thus, in an exemplary embodiment, the multiuse device includes a first body interface, wherein the housing is releasable supported by the first body interface, and the housing is configured to be used as an off the ear (OTE) sound processor of the hearing prosthesis without the first body interface.

Again, in some embodiments, the housing is a housing of a smartwatch.

In some embodiments, the multiuse device is configured to automatically provide different functionality depending on what part of the body on which the housing is worn. This can be a result of the ability of the multiuse device to determine where the housing is located due to the interaction with various components that enable the housing to be located at the various parts of the body (e.g., a sensor arrangement associated with the wristband, a sensor arrangement that can determine that the housing is interfacing with the magnetic field of the implanted component, etc.). This can also be a result of the ability of the multiuse device to determine where the housing is located irrespective of whether or not the housing is interfacing with other support components (e.g., the housing can tell where on the body it is located via biometric sensors, accelerometers, etc.). Any device, system and/or method that can enable the multiuse device to automatically provide different functionality depending on what part of the body to which the housing is worn can be utilized in at least some exemplary embodiments.

In an exemplary embodiment, there is a multiuse device, comprising: a housing; a wristband; and a mobile operating system supported by the housing, wherein the multiuse device is a smartwatch configured to be worn on a wrist of a recipient of a hearing prosthesis and secured thereto by the wristband; and the multiuse device is configured to interact with a hearing prosthesis.

In an exemplary embodiment, there is a device as described above and/or below, wherein the multiuse device is configured to receive input from the recipient and control the hearing prosthesis based on the input.

In an exemplary embodiment, there is a device as described above and/or below, wherein the multiuse device is configured to provide backup functionality to the hearing prosthesis.

In an exemplary embodiment, there is a device as described above and/or below, wherein the multiuse device is configured to operate as a wireless accessory to the hearing prosthesis.

In an exemplary embodiment, there is a device as described above and/or below, wherein the multiuse device is configured such that the housing is operationally releasable from the wristband; and the housing is configured to be held against skin of a recipient via a magnetic field generated by at least one of an implanted magnet or a magnet supported by the housing.

In an exemplary embodiment, there is a device as described above and/or below, wherein the device communicates with the hearing prosthesis utilizing non-inductance communication.

In an exemplary embodiment, there is a device as described above and/or below, wherein the device is a back-up sound processor for the hearing prosthesis.

It is further noted that any disclosure of a device and/or system detailed herein also corresponds to a disclosure of otherwise providing that device and/or system.

It is further noted that any element of any embodiment detailed herein can be combined with any other element of any embodiment detailed herein unless stated so providing that the art enables such. It is also noted that in at least some exemplary embodiments, any one or more of the elements of the embodiments detailed herein can be explicitly excluded in an exemplary embodiment. That is, in at least some exemplary embodiments, there are embodiments that explicitly do not have one or more of the elements detailed herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A body worn device, comprising:
   a chassis; and
   a functional suite supported by the chassis, wherein
   the device is configured to be worn on a recipient of a prosthesis, and
   the device is configured such that the functional suite automatically provides second functionality when the chassis is removed from the body of the recipient, the second functionality being related to the prosthesis.

2. The body worn device of claim 1, wherein:
   the chassis is a chassis of a smartwatch.

3. The body worn device of claim 1, wherein:
   the second functionality is a remote microphone functionality of the prosthesis, wherein the device is configured to communicate a signal indicative of a captured sound captured by the body worn device to the prosthesis.

4. The body worn device of claim 1, wherein:
   the second functionality is a functionality of an OTE sound processor; and
   at least one of the chassis or a component supported by the chassis is a ferromagnetic material such that the chassis can be held against skin of the recipient via an implanted magnet implanted in the recipient.

5. The body worn device of claim 1, wherein:
   the device is configured to automatically prompt a wearer for input as to whether the second functionality is desired.

6. The body worn device of claim 1, wherein:
   the body worn device is configured to wirelessly communicate with an implanted component of the recipient.

7. The body worn device of claim 1, wherein:
   the device is a consumer electronics device.

8. The body worn device of claim 1, wherein:
the device is separate from the prosthesis.

9. The body worn device of claim 1, wherein:
the device is configured to implement the second functionality without the prosthesis.

10. The body worn device of claim 1, wherein:
a functionality of the functional suite separate from the second functionality is conveyance of visual information to the recipient; and
the second functionality is a generation of a signal, the signal being of a kind that can transcutaneous communicate with the prosthesis.

11. The body worn device of claim 1, wherein:
the device is configured to implement a functionality of the functional suite separate from the second functionality without the prosthesis.

12. The body worn device of claim 1, wherein:
device is configured to be worn away from a head of a recipient; and
the prosthesis is a hearing prosthesis.

13. The body worn device of claim 1, wherein:
the second functionality is an inductance communication functionality, the inductance communication functionality being a functionality enabling transcutaneous communication with the prosthesis, wherein the second functionality is previously deactivated prior to the automatically providing of the second functionality.

14. The body worn device of claim 1, wherein:
the chassis has a generally rectangular shape.

15. A system, comprising:
the body worn device of claim 1; and
the prosthesis, wherein the prosthesis includes an implantable portion and an external portion.

16. A method, comprising:
utilizing a body wearable consumer electronics device as a head worn device to at least one of control or provide a signal to a prosthesis; and
utilizing a processor in the body wearable device to perform functions unrelated to the prosthesis while wearing the device on a portion of the body other than the head.

17. The method of claim 16, wherein:
the action of utilizing the processor to perform functions unrelated to the prosthesis is executed while using a primary body wearable device of the prosthesis to at least one of control or provide a signal to the prosthesis, wherein the primary body wearable device is one of a BTE device or an OTE sound processor, and the consumer electronics device is different therefrom.

18. The method of claim 16, wherein:
the action of utilizing the processor to perform functions unrelated to the prosthesis is executed at least once a day for a week before the action of using the body wearable device to at least one of control or provide a signal to the prosthesis.

19. The method of claim 16, wherein:
the method further includes utilizing the consumer electronics device to access the internet; and
the method further includes wirelessly communicating with and thereby interacting with a different in kind consumer electronics device, wherein the different in kind consumer electronics device is a smart phone.

20. The method of claim 16, wherein:
the action of using the processor to perform functions unrelated to the prosthesis includes using the consumer electronics device as a smartwatch while worn on a wrist of the recipient.

21. The method of claim 16, wherein:
the action of utilizing the consumer electronics device as a head worn device includes utilizing the consumer electronics device as a remote mini-microphone.

22. The method of claim 16, wherein:
the action of utilizing the consumer electronics device as a backup device as a head worn device consists of utilizing the consumer electronics device when a component of the prosthesis is functionally unavailable to at least partially achieve the functionality of the component.

* * * * *